United States Patent [19]

Failli et al.

[11] 4,000,122

[45] * Dec. 28, 1976

[54] NOVEL HYDRAZINOCARBOXAMIDE DERIVATIVES AND PREPARATION THEREOF

[75] Inventors: Amedeo Failli, Montreal; Verner R. Nelson, Kirkland; Hans U. Immer, Montreal; Manfred K. Gotz, Hudson, all of Canada

[73] Assignee: American Home Products Corporation, New York, N.Y.

[ * ] Notice: The portion of the term of this patent subsequent to June 10, 1992, has been disclaimed.

[22] Filed: Apr. 7, 1975

[21] Appl. No.: 565,332

Related U.S. Application Data

[62] Division of Ser. No. 330,359, Feb. 7, 1973, Pat. No. 3,888,840.

[52] U.S. Cl. .................... 260/112.5 R; 424/177
[51] Int. Cl.² .............. C07C 103/52; A61K 37/00
[58] Field of Search ..................... 260/112.5 R

[56] References Cited

UNITED STATES PATENTS 3,888,840   6/1975   Failli et al. ............... 260/112.5 R

OTHER PUBLICATIONS

I. Ugi, "Newer Methods of Preparative Organic Chemistry", vol. IV, W. Foerst, ed., Academic Press, N.Y. (1968), p. 30.
Gokel et al., "Isonitrile Chemistry", I. Ugi, ed., Academic Press, N.Y. (1971), pp. 159–61.

*Primary Examiner*—Lewis Gotts
*Assistant Examiner*—Reginald J. Suyat
*Attorney, Agent, or Firm*—Stephen Venetianer

[57] ABSTRACT

α-Hydrazinocarboxamide and α-(α'-acylhydrazino)-carboxamide derivatives of formula I

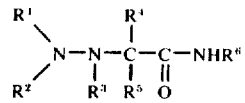

in which $R^1$ and $R^2$ each are lower alkyl or $R^1$ and $R^2$ together with the nitrogen atom to which they are joined form a piperidino or morpholino radical; $R^3$ is hydrogen, lower alkanoyl, benzoyl, p-nitrobenzoyl, p-aminobenzoyl, p-chlorobenzoyl, isocyanoacetyl, or protected amino acyl radicals, for example, N-formylglycyl or

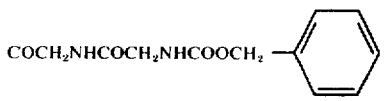

(N-carbobenzoxyglycylglycyl); $R^4$ is lower alkyl, $CHR^7COOR^8$ or $CH_2CH_2COOR^8$ wherein $R^7$ is hydrogen or phenyl and $R^8$ is hydrogen or lower alkyl; $R^5$ is hydrogen or lower alkyl; or $R^4$ and $R^5$ together with the carbon atom to which they are joined form a cyclohexylidene radical; and $R^6$ is a cyclohexyl or $CHR^9COY$ wherein $R^9$ is hydrogen or benzyl and Y is hydroxyl, lower alkoxy or amine, with the provisos that when Y is hydroxyl then $R^8$ is hydrogen, that when Y is lower alkoxy than $R^8$ is lower alkyl and that when Y is amino $R^4$ is lower alkyl, are disclosed herein along with the related α-hydrazino-carboxamide and α-(α'-acylhydrazino)carboxamide compounds of formula III

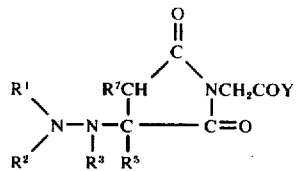

in which $R^1$, $R^2$, $R^3$, $R^5$ and $R^7$ are as defind above and Y is lower alkoxy. These compounds possess antibacterial activity. Methods for their preparation and use are disclosed also.

10 Claims, No Drawings

NOVEL HYDRAZINOCARBOXAMIDE DERIVATIVES AND PREPARATION THEREOF

This is a division of application Ser. No. 330,359 filed Feb. 7, 1973 now U.S. Pat. No. 3,888,840.

BACKGROUND OF THE INVENTION

1. Field of Invention

This invention relates to novel α-hydrazinocarboxamide and α-(α'-acylhydrazino)carboxamide derivatives, to processes for their preparation and to their use as intermediates for the preparation of related derivatives.

2. Description of the Prior Art

Only within the last ten years has some attention been focused on α-hydrazinocarboxamides. This attention resulted from a chemical investigation by I. Ugi and F. Bodesheim, Justus Liebigs Ann. Chem., 666, 61 (1963). In this particular investigation α-(α', β'-diacylhydrazino)carboxamides were prepared by the α-addition of acylhydrazones and carboxylic acids to isonitriles. The carboxamides of this latter study are readily distinguished from the compounds of the present invention by their lack of a basic nitrogen.

Indeed, the successful preparation of the present α-(hydrazino)- and α-(α'-acylhydrazino)caboxamides from hydrazones, acids and isonitriles is somewhat unexpected and surprising in light of a recent comment by Ugi. More explicitly, in "Newer Methods of Preparative Organic Chemistry", Vol. IV, N. Foerst, Ed., Academic Press, New York and London, 1968, p. 28, Ugi states that the lower basicity of the α-nitrogen in a hydrazone system has an adverse influence on α-additions involving hydrazones and it may be assumed that such reactions can rarely be used for preparative purposes.

SUMMARY OF THE INVENTION

The α-hydrazinocarboxamide derivatives of the present invention may be represented by Formula I,

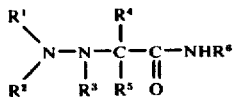

in which $R^1$ and $R^2$ each are lower alkyl or $R^1$ and $R^2$ together with the nitrogen atom to which they are joined form a piperidino or morpholino radical; $R^3$ is hydrogen, lower alkanoyl, benzoyl, p-nitrobenzoyl, p-aminobenzoyl, p-chlorobenzoyl, isocyanoacetyl, or protected amino acyl radicals, for example, N-formylglycyl or

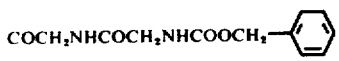

(N-carbobenzoxyglycylglycyl); $R^4$ is lower alkyl, $CHR^7COOR^8$ or $CH_2CH_2COOR^8$ wherein $R^7$ is hydrogen or phenyl and $R^8$ is hydrogen or lower alkyl; $R^5$ is hydrogen or lower alkyl; or $R^4$ and $R^5$ together with the carbon atom to which they are joined form a cyclohexylidene radical; and $R^6$ is a cyclohexyl or $CHR^9COY$ wherein $R^9$ is hydrogen or benzyl and Y is hydroxyl, lower alkoxy or amino, with the provisos that when Y is hydroxyl then $R^8$ is hydrogen, that when Y is lower alkoxy then $R^8$ is lower alkyl and that when Y is amino $R^4$ is lower alkyl.

In one aspect of this invention the preparation of the compounds of formula I involve a key reaction wherein a hydrazone of formula II in which $R^1$, $R^2$ and $R^5$ are as defined hereinbefore and $R^4$ is lower alkyl, $CHR^7COOR^8$ or $CH_2CH_2COOR^8$ wherein $R^7$ is as defined hereinbefore and $R^8$ is lower alkyl or $R^4$ or $R^5$ together with the carbon atom to which they are joined form a cyclohexylidine radical, is treated with an acid of formula $R^3X$ in which $R^3$ is as defined hereinbefore and when $R^3$ is hydrogen, $R^3$ and X together represent an inorganic acid ionizable to provide a proton, and when $R^3$ is other than hydrogen as defined hereinbefore X represents a hydroxyl, in the presence of an isonitrile of formula $R^6NC$ in which $R^6$ is cyclohexyl or $CHR^9COY$ wherein $R^9$ is as defined hereinbefore and Y is lower alkoxy to obtain the corresponding compound of formula I

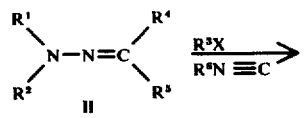

In another aspect of this invention compounds of formula I in which $R^1$, $R^2$, $R^3$ and $R^5$ are as defined in the first instance, $R^4$ is $CHR^7COOR^8$ in which $R^7$ is as defined hereinbefore and $R^8$ is lower alkyl and $R^6$ is $CH_2COY$ in which Y is lower alkoxy are transformed to 2,5-dioxopyrrolidines of formula III either spontaneously during the formation of said latter compounds of formula I or by subjecting said latter compounds of formula I to alkaline conditions.

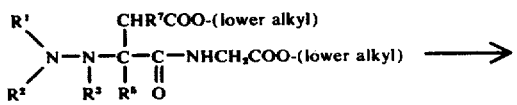

I [($R^4$ = $CHR^7COO$-(lower alkyl) and $R^6$ = $CH_2COO$-(lower alkyl))]

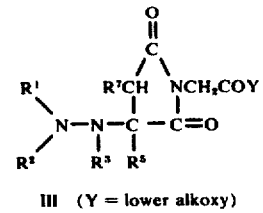

III (Y = lower alkoxy)

DETAILED DESCRIPTION OF THE INVENTION

The term "lower alkyl" as used herein contemplates straight chain alkyl radicals containing from one to six carbon atoms and branched chain alkyl radicals containing three to four carbon atoms and includes methyl, ethyl, propyl, isopropyl, butyl, isobutyl, pentyl and the like.

The term "lower alkanoyl" as used herein contemplates both straight and branched chain alkanoyl radicals containing from one to six carbon atoms and includes formyl, acetyl, propionyl, hexanoyl and the like.

The term "lower alkoxy" as used herein contemplates both straight and branched chain alkoxy radicals containing from one to six carbon atoms and includes methoxy, ethoxy, propoxy, hexyloxy and the like.

It will be noted that the structure of the compounds of this invention includes asymmetric carbon atoms. It is to be understood accordingly that the isomers arising from this asymmetry are included within the scope of this invention. Such isomers are obtained by classical separation techniques and by sterically-controlled synthesis.

The compounds of formula 1 of this invention exhibit utility as antibacterial agents against a number of microorganisms, for example, Pseudomonas aeruginosa, Proteus mirabilis, Proteus vulgaris, Klebsiella pneumoniae and Serratia marcescens, in standard tests for antibacterial activity, such as those described in "Antiseptics, Disinfectants, Fungicides and Sterilization", G.F. Reddish, Ed., 2nd ed., Lea and Febiger, Philadelphia, 1957 or by D.C. Grove and W.A. Randall in "Assay Methods of Antibiotics", Med. Encyl. Inc., New York 1955.

For example, a test like the serial broth dilution, see Grove and Randall, cited above, in which dilutions of the compounds of this invention in nutrient broth are inoculated with the mircroorganisms or fungi, described above, incubated at 37° C. for 2 days, respectively, and examined for the presence of growth, shows that 3-[N-(dimethylamino)formamido]-3-methyl-2,5-dioxo-1-pyrrolidineacetic acid ethyl ester (Example 27) is able to inhibit growth totally in this system of Proteus vulgaris, Klebsiella pneumoniae and Serratia marcescens at a concentration of 100 mcg/ml. or less.

When the compounds of formula 1 are employed as antibiotic or antifungal agents in warm-blooded animals, e.g. rats, they may be administered alone or in combination with pharmacologically acceptable carriers. The proportion of the compound is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present compounds as antibiotic agents will vary with the form of administration and the particular compound chosen. Furthermore, it will vary with the particular compounds chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford antibacterially or antifungally effective results without causing any harmful or deleterious side effects and preferably at a level that is in a range of from about 1.0 mg to about 1000 mg. per kilo per day, although as aforementioned variations will occur. However, a dosage level that is in the range of from about 10 mg to about 500 mg per kilo per day is most desirably employed in order to achieve effective results.

In addition, the said ultimate products may be employed topically. For topical application they may be formulated in the form of solutions, creams, or lotions in pharmaceutically acceptable vehicles containing 0.1–5 per cent, preferably 2 per cent, of the agent and may be administered topically to the infected area of the skin.

Also the antibacterial properties of the said ultimate products may be utilized for washing equipment in hospitals, homes and farms, instruments used in medicine and bacteriology, clothing used in bacteriological laboratories, and floors, walls and ceilings in rooms in which a background free of gram-positive and gram-negative microorganisms, such as those listed above, is desired. When employed in this manner the said ultimate products are formulated in a number of compositions comprising the active compound and an inert material. In such compositions, while the said ultimate products may be employed in concentrations as low as 500 p.p.m., from a practical point of view, it is desirable to use from about 0.1% to about 5% by weight or more.

The formulations that may be used to prepare antiseptic wash solutions of the compounds of this invention are varied and may readily be accomplished by standard techniques, see for example, "Remington's Practice of Pharmacy", E.W. Martin et al., Eds., 12th ed., Mack Publishing Company, Easton, Penn., 1961, pp. 1121–1150. In general, the said ultimate products are made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g., up to about 5% by weight, of the compounds may be formulated by conventional techniques.

A typical antiseptic preparation useful for disinfecting floors, walls, ceiling, and articles in a contaminated room may be prepared by adding 5 to 25 g. of 3-[N-(dimethylamino)formamido]-3-methyl-2,5-dioxo-1-pyrrolidine-acetic acid ethyl ester to a mixture of 150 to 300 g of polyethylene glycol 1540 and 150 to 300 g of polyethylene glycol 300. The resulting mixture is stirred while a solution of 1 to 10 g of sodium lauryl sulfate in 300 to 400 ml of water is added portionwise. The article to be disinfected is coated or immersed in the preparation for a prolonged time, for example, one hour, and then rinsed with sterile water.

In addition, the compounds of formula 1 exhibit trichomonacidal activity against certain Trichomonas species, for example, Trichomonas vaginalis. A demonstration of this activity is readily achieved in standard tests for trichomonacidal activity; for example, see R.J. Schnitzer in "Experimental Chemotherapy", Vol. 1, R.J. Schnitzer and F. Hawking, Ed., Academic Press, New York, 1963, p. 289.

When the compounds of formula 1 are employed as trichomonocidal agents they may be administered in the same manner described above for their application as antibacterial agents.

Likewise, the 2,5-dioxopyrrolidines of formula 111 exhibit a similar degree of the antibacterial and trichomonacidal activities, described above. Accordingly, they may be used for this purpose in the same manner as described for the compounds of formula 1.

In practising the process of this invention three classes of starting material are required; namely, hydrazones of formula 11, acids of formula $R^3X$ and isonitriles of formula $R^6NC$.

The requisite hydrazones of formula 11 are prepared by condensing an appropriately substituted hydrazine of formula $R^1R^2NNH_2$ in which $R^1$ and $R^2$ are as defined in the first instance, with a carbonyl compound of formula $R^4R^5CO$ in which $R^4$ is lower alkyl, $CHR^7COOR^8$ or $CH_2CH_2COOR^8$ wherein $R^7$ is hydrogen or phenyl and $R^8$ is lower alkyl and $R^5$ or $R^4$ and $R^5$ together are as defined hereinbefore.

Hydrazines of formula $R^1R^2NNH_2$ are either known for example, 1,1-dimethyl hydrazine, N-aminopiperidine, N-aminomorpholine, or they are prepared by known methods; for example, see E. Muller in "Methoden der Organischen Chemie", Houben-Weyl, E. Muller, Ed., Vol. 10/2, Georg Thieme Verlag, Stuttgard, 1967, p. 50.

Likewise, the carbonyl compounds of formula $R^4R^5CO$ are known and most are commercially available, for example, ethyl acetoacetate, isobutyraldehyde and cyclohexanone, or are prepared by known methods; for example, see P. Karrer, "Organic Chemistry", 2nd ed., Elsevier Publishing Co., Inc., New York, 1946, p. 149.

The condensation of the hydrazine of formula $R^1R^2NNH_2$ and the carbonyl compound of formula $R^4R^5CO$ is preferably carried out in an inert solvent at an elevated temperature, at or near the reflux temperature of the mixture. Either an anhydrous, water-immiscible hydrocarbon solvent, for example, benzene or toluene, with concomitant physical removal of water as it is being formed, e.g. by means of a Dean-Stark water separator, or a lower alkanol solvent, for example, ethanol, propanol or isopropanol may be employed. Thereafter, evaporation of the solvent and purification of the residue, for example, by distillation or crystallization, yields the corresponding hydrazone of formula 11.

The acids of formula $R^3X$ are known and are commercially available and include the inorganic acids, hydrochloric, sulfuric, phosphoric, hydrobromic acid and the like, or the organic acids, formic, acetic, benzoic, p-nitrobenzoic and the like.

The requisite isonitriles of formula $R^6NC$ also are known, for example, cyclohexyl isonitrile [(I. Ugi and R. Meyr, Ber., 93, 239 (1960)] and ethyl isocyanoacetate [R. Appel et al., Angew. Chem., Int. ed., 10, 132 (1971)], or are easily prepared by known methods, for example, see P. Hoffmann, et al., in "Isonitrile Chemistry", Organic Chemistry, Vol. 20, I. Ugi, Ed., Academic Press, New York, 1971, p. 9.

Next, in a key reaction of the process of this invention, the aforementioned hydrazone of formula 11 is condensed with the acid of formula $R^3X$, and the isonitrile of formula $R^6NC$, described above, to yield the corresponding compounds of formula 1.

Although not critical it is preferable to use approximately equimolar amounts of the three requisite starting materials, for this condensation. The condensation is effected most conveniently in an inert solvent, for example, halogenated hydrocarbons including methylene dichloride, chloroform, and carbon tetrachloride, ethers and cyclic ethers including dioxane, diethyl ether and tetrahydrofuran, or lower aliphatic alcohols including methanol, ethanol and propanol. However, when the three starting materials are mutually soluble or the mixture thereof becomes liquid during the course of the condensation the solvent may be omitted without any deleterious effects.

The temperature and duration of the condensation also are not critical. The reaction may be performed at temperatures ranging from −20° to 100° C.; however, a range from 10° to 40° C is most convenient, with room temperature to the boiling point of the solvent employed being preferred. The reaction time varies widely and depends on the reactivity of the various starting materials; however, reaction times from 15 minutes to several days are employed generally, with six hours to two days being preferred.

Thereafter the product is isolated and purified according to standard procedures. For instance the product is extracted with a water-immiscible solvent and, if needed, purified by chromatography and crystallization.

In this manner there are obtained the compounds of formula 1 in which $R^1$, $R^2$, $R^3$ and $R^5$ are defined in the first instance, $R^4$ is lower alkyl, $CHR^7COOR^8$ or $CH_2CHCOOR^8$ wherein $R^7$ is hydrogen or phenyl and $R^8$ are lower alkyl or $R^4$ and $R^5$ together with the carbon atom to which they are joined form a cyclohexylidene radical, and $R^6$ is cyclohexyl or $CHR^9COY$ in which $R^9$ is as defined hereinbefore and Y is lower alkoxy.

As noted hereinbefore the compounds of formula 1 in which $R^1$, $R^2$, $R^3$ and $R^5$ are as defined in the first instance, $R^4$ is $CHR^7COOR^8$ in which $R^7$ is as defined hereinbefore and $R^8$ is lower alkyl and $R^6$ is $CHR^9COY$ in which $R^9$ is hydrogen and Y is lower alkoxy are transformed to the corresponding 2,5-dioxopyrrolidines of formula 111. This transformation takes place spontaneously to some extent (10–80%) during the course of the condensation of the hydrazone of formula $R^1R^2NN = C(R^5)CH_2COOR^8$ in which $R^1$, $R^2$ and $R^5$ are as defined herein and $R^8$ is lower alkyl, with a lower alkyl ester of isocyanoacetic acid and an acid of formula $R^3X$ as defined herein under the conditions described above for such condensations. The mixture of the corresponding products of formulae 1 and 111 obtained under these conditions may be separated by crystallization or chromotagraphy on silica gel. If desired, the mixture is readily converted totally to the corresponding compound of formula 111 by treating the mixture with a base, for example, the alkali metal carbonates including sodium or potassium carbonate or the alkali metal hydroxides including sodium or potassium hydroxide in an inert solvent, for example, chloroform, benzene, tetrahydrofuran or ethanol. Completion of this conversion under alkaline conditions is achieved usually at temperatures ranging from 20° to 100° C, preferably 50° to 60° C., and reaction times of from 10 minutes to 6 hours, preferably one to two hours.

The compounds of formula 1 in which $R^4$ is $CHR^7COOR^8$ or $CH_2CH_2COOR^8$ wherein $R^7$ is as defined hereinbefore and $R^8$ is hydrogen and $R^6$ is $CHR^9COY$ in which $R^9$ is as defined hereinbefore and Y is hydroxyl, mainly, the corresponding acid derivatives of the aforementioned esters, are obtained by treatment of said corresponding esters with a hydrolyzing agent. Generally speaking, this conversion is most conveniently performed by employing a base as the hydrolyzing agent, although hydrolysis under acidic conditions is also applicable. It should be noted herein that when compounds of formula 1 in which $R^4$ is $CHR^7COOR^8$ in which $R^8$ is lower alkyl and $R^6$ is $CH^9COY$ in which Y is lower alkoxy are subjected to the above hydrolyzing conditions a mixture of the corresponding diacid and 2,5-dioxopyrrolidine of formula 1 results.

For basic hydrolysis a preferred embodiment involves subjecting the lower alkyl ester to the action of a strong base, for example, sodium or potassium hydroxide, in the presence of sufficient water to effect hydrolysis of the ester. The hydrolysis is performed using a suitable solvent, for example, methanol or ethanol.

The reaction mixture is maintained at a temperature of from 0° C to the reflux temperature until hydrolysis occurs. Usually from 10 minutes to six hours is sufficient for this hydrolysis. The reaction mixture is then rendered acidic with an acid, for example, acetic acid, hydrochloric acid, sulfuric acid and the like, to obtain the corresponding free acid.

The compounds of formula 1 in which $R^4$ is lower alkyl and $R^6$ is $CHR^9COY$ in which $R^9$ is as defined hereinbefore and Y is amino are obtained by treatment of the corresponding lower alkyl esters, described above, with ammonia according to standard amidation methods. Preferred conditions for this amidation include treatment of the appropriate ester of formula 1 with a saturated solution of ammonia in an inert solvent, for examle, methanol, ether or tetrahydrofuran at 0° to 20° C for 6 hours to 5 days.

The compounds of formula 1 in which $R^3$ is p-aminobenzoyl are obtained by treating the corresponding compounds of formula 1, described above, in which $R^3$ is p-nitrobenzoyl with a reducing agent. In this case the use of hydrogen in the presence of a noble metal catalyst, for example, palladium, platinum and the like in a hydrogenation apparatus is a preferred and convenient method.

Finally, the compounds of formula 1 in which $R^3$ is isocyanoacetyl ($COCH_2NC$) are prepared directly from the aforementioned, corresponding compounds of formula 1 in which $R^3$ is N-formylglycyl. This transformation is effected readily with dehydrating agents known to be effective for transforming known formamides to corresponding isonitriles, see P. Hoffmann, et al., cited above. A preferred method in this case is the use of phosgene in the presence of triethylamine.

The following examples illustate further this invention.

EXAMPLE 1

Ethyl Levulinate Dimethyl Hydrazone

A mixture of 21.5 g (0.15 mole) of ethyl levulinate and 15.0 g (0.25 mole) of anhydrous dimethylhydrazine in 35 ml of ethanol is heated at reflux for 4 hours. The solvent is removed and the residue fractionally distilled. The title compound is collected, b.p. 98°–100° C/15 mm., nmr (CDCl$_3$ δ1.25 ($t$, J=7,3H), 1.95 (3H), 2.40 (6H), 2.53 (4H), 4.13 (q, J=7,2H).

In the same manner but replacing ethyl levulinate with an equivalent amount of ethyl acetoacetate, ethyl acetoacetate dimethyl hydrazone, b.p. 88°–92° C/19–20 mm, $\nu_{max}^{CHCl}$ 3245, 3180 and 1728 cm$^{-1}$, is obtained.

Similar replacement of the ethyl levulinate with ethyl αphenylacetoacetate gives ethyl α-phenylacetoacetate dimethyl hydrazone, b.p. 138°–143° C/5 mm, nmr (CDCl$_3$) δ 1.13 and 1.30 (2t, J = 7, 3H), 1.47 (3H), 1.56(3H), 1.86 (3H).

Similar replacement of the ethyl levulinate with cyclohexanone gives cyclohexanone dimethyl hydrazone, b.p. 80°–82° C/25 mm, nmr (CDCl$_3$) δ 1.66 (6H), 2.43 (10H).

Similar replacement of the ethyl levulinate with 2-oxocyclohexanecarboxylic acid ethyl ester gives 2-oxocyclohexanecarboxylic acid ethyl ester dimethyl hydrazone, b.p.132° C/11mm.

EXAMPLE 2

3-(Piperidinoimono)butyric Acid Methyl Ester

A mixture of methyl acetoacetate (13 g. 0.10 mole) and 1-aminopiperidine (15 g, 0.15 mole) in absolute ethanol (30 ml) is heated at reflux for 4 hr. The solvent is removed and the residue fractionally distilled. The title compound has b.p. 125°–126° C/13 mm.

In the same manner but replacing 1-aminopiperidine with an equivalent amount of 1-aminomorpholine, 3-(morpholinoimino)butyric acid ethyl ester, b.p. 150°–152° C/20 mm, $\nu_{max}^{CHCl}$ 3240, 3180, 1720, 1640, 1600 cm$^{-1}$, is obtained.

In the same manner but replacing ethyl acetoacetate with an equivalent amount of cyclohexanone, 1-(cyclohexylideneamino)piperidine, b.p. 124°–217° C/15-18 mm, is obtained. Reported b.p. for this compound is 76° C/0.4 mm, h. Boehlke and W. Kliegel, Arch. Pharm. 229, 245 (1966).

EXAMPLE 3

Isobutyraldehyde Dimethyl Hydrazone

A solution of isobutyraldehyde (43 g. 0.6mole) and dimethylhydrazine (60 g, 1.0 mole) in benzene (500 ml) is heated at reflux temperature for 5 hr. using a Dean-Stark apparatus to collect the water. The solution is evaporated and the residue fractionally distilled. The hydrazone is obtained as a yellow oil, b.p. 120° C, $\nu_{max}^{Film}$ 1610, 1475, 1450 cm$^{-1}$.

In the same manner but replacing isobutyraldehyde with an equivalent amount of isovaleraldehyde, isovaleraldehyde dimethyl hydrazone, b.p. 145° –149° C is obtained.

Similar replacement of the isobutyraldehyde with an equivalent amount of propionaldehyde or hexaldehyde gives propionaldehyde dimethyl hydrazone and hexaldehyde dimethyl hydrazone, respectively.

EXAMPLE 4

2-Isocyano-3-phenylpropionic Acid Methyl Ester

A solution of phosgene (5.2 g, 0.052 mole) in dry methylene chloride (45 ml) is added dropwise to a stirred solution of N-formylphenylalanine methyl ester (10.0 g, 0.048 mole) and 1-methylmorpholine (13 g, 0.125 mole) in dry methylene chloride (25 ml) at −30° C. After completion of the addition the filtrate is concentrated under reduced pressure at room temperature. Benzene is added to the residue followed by filtration and concentration of the resulting solution. The residue is distilled to afford the title compound as a yellow oil, b.p. 97° C/0.3 mm, $\nu_{max}^{CHCl}$ 2150, 1746, 1595, 1578, 1489, 694 cm$^{-1}$.

The starting material, N-formylphenylalanine methyl ester, is known; see R.G. Jones, J. Amer. Chem. Soc., 71, 644 (1949) for D L-form and F. Bergel, et al., J. Chem. Soc., 3802 (1962) for L-form.

In the same manner but replacing the preceding starting material with an equivalent amount of N-formylmethionine ethyl ester, described in German Pat. No. 1,201,357, issued September 23, 1965 [Chem. Abstr.

63, 18260 (1965)], 2-isocyano-4-methylthiobutyric acid ethyl ester, b.p. 77°–79° C/ 0.1 mm, is obtained.

EXAMPLE 5

N-cyclohexyl-3-(dimethylaminoformamido)-3-methylglutaramic Acid Ethyl Ester (1; $R^1$ and $R^2$ = $CH_3$, $R^3$ = CHO, $R^4$ = $CH_2CH_2COOC_2H_5$, $R^5$ = $CH_3$ and $R^6$ = cyclohexyl)

A solution of the hydrazone of formula II, ethyl levulinate dimethyl hydrazone (9.39 g, 0.05 mole), described in Example 1, and the isonitrile of formula $R^6NC$, cyclohexyl isonitrile (5.45 g, 0.05 mole), in 10 ml of dry methylene dichloride is cooled in an ice bath and treated dropwise with the acid of formula $R^3X$, formic acid (2.35 g, 0.05 mole). The mixture is stirred for 20 minutes in the cold and then stirred at room temperature until completion of the condensation. [In this case the condensation is complete after 3 hr. as determined by thin layer chromatography (tlc) using silica gel plates and a solvent system consisting of benzene-ethyl acetate (1:1)]. The reaction mixture is diluted with 4N sodium hydroxide and extracted with ethyl acetate. The extract is washed with water until neutral, dried ($MgSO_4$) and evaporated yielding a solid residue. The residue is crystallized from methylene dichloride-hexane to yield the title compound, m.p. 81.5°–83° C., $\nu_{max}^{CHCl}$ 3455, 3340, 1727, 1507 $cm^{-1}$.

EXAMPLE 6

N-[N-(Dimethylamino)-N-(N-formylglycyl)]-Dl-valyl glycine Ethyl Ester (1; $R^1$ and $R^2$ = $CH_3$; $R^3$ = $COCH_2NHCHO$, $R^4$ = $CH(CH_3)_2$, $R^5$ = H and $R^6$ = $CH_2COOC_2H_5$)

The acid of formula $R^3X$,N-formylglycine (15.4 g), described by R.S. Tipson and B.A. Pawson, J. Org. Chem., 26, 4698 (1961), is added dropwise to a solution of the hydrazone of formula 11, isobutyraldehyde dimethyl hydrazone (17.1 g), described in Example 3, and the isonitrile of formula $R^6NC$, ethyl isocyanoacetate (16.0 g), in 50 ml of anhydrous methanol containing 20 g. of hydrated alkali-aluminum silicate (Molecular Sieves No. 4), cooled to 0° C. The mixture is stirred at room temperature until completion of the condensation. [In this case the condensation is complete after 24 hr. as determined by tlc using silica gel plates and a solvent system consisting of ethyl acetate-methanol (9:1)]. The mixture is filtered and concentrated. The residue is subjected to chromatography on silica gel. Elution with ethyl acetate-methanol (9:1) gives the title compound, nmr ($CDCl_3$) δ 0.91 and 1.02 (2d, J=6.5, 6H), 1.27 (t, J=7, 3H), 2,53 (3H), 2.56 (3H), 3.03 (m, 1H), 3.44 (d, J = 11, 1H), 3.97 (2H), 4.20 (q, J = 7, 2H), 4.35 (2H), 6.62 (1H).

EXAMPLE 7

N-[(N-Dimethylamino)-DL-valyl]glycine Ethyl Ester (1, $R^1$ and $R^2$ = $CH_3$, $R^3$ = H,$R^4$ = $CH(CH_3)_2$, $R^5$ = H and $R^6$ = $CH_2COOC_2H_5$)

A solution of the hydrazone of formula 11, isobutyraldehyde dimethylhydrazone (19.6 g, 0.172 mole) described in Example 3, water (17.2 ml), and methanol (28.6 ml) is stirred at ice-bath temperature. After 5 min., 12N HCl (14.5 ml) is added slowly. After an additional 2 min. the isonitrile, ethyl isocyanoacetate (19.4 g, 0.172 mol) is added. The solution is stirred at room temperature for 1.5 hr. The solution is diluted with methylene chloride (500 ml), and washed with 4N $NH_4OH$ (100 ml), water (50 ml), and a saturated solution of sodium chloride (100 ml). The organic phase is dried ($Na_2SO_4$) and concentrated. The orange oil is distilled to yield the title compound, b.p. 124° C/0.1 mm, $\nu_{max}^{CHCl}$ 3380, 1730, 1660, 1510 $cm^{-1}$.

By following the procedure of Example 5, 6 or 7 and using the appropriate hydrazone of formula 11, acid of formula $R^3X$ and isonitrile of formula $R^6NC$ then other compounds of formula II are obtained. Examples of such compounds of formula I are listed in Table I together with the hydrazone, acid and isonitrile required for their preparation.

TABLE 1

| Ex. | Hydrazone of Formula 11 | Acid of Formula $R^3X$ | Isonitrile ($R^6NC$) | Product of Formula 1 |
|---|---|---|---|---|
| 8 | ethyl aceto-acetate dimethyl hydrazone | formic acid | cyclohexyl isonitrile | N-cyclohexyl-3-(dimethyl-aminoformamido)-3-methylsuccinamic acid ethyl ester, m.p. 79.5 – 81° C, $\nu_{max}CHCl_3$ 1728, 1668 $cm^{-1}$. |
| 9 | ethyl levulinate dimethyl hydrazone | benzoic acid | cyclohexyl isonitrile | N-cyclohexyl-4-[N-(dimethylamino)benzamido]-4-methylglutaramic acid ethyl ester, m.p. 79 – 80.5° C, $\nu_{max}CHCl_3$ 1728, 1665, 1650 $cm^{-1}$. |
| 10 | ethyl aceto-acetate dimethyl hydrazone | formic acid | 2-isocyano-3-phenylpropionic acid methyl ester (described in Example 4) | N-(α-carboxyphenethyl)-3-[N-(dimethylamino)-formamido]-3-methyl-succinamic acid ethyl N-methyl diester, m.p. 91 – 109° C, nmr ($CDCl_3$) δ 1.24 (+, J=7,3H), 2.78 (6H), 2.82 (m,2H), 3.17 (d, J=6.5, 2H) |
| 11 | isobutyraldehyde dimethyl hydrazone | formic acid | 2-isocyano-3-phenylpropionic acid methyl ester | N-[N-(dimethylamino)-N-formyl-DL-valyl]phenyl-alanine methyl ester, $\nu_{max}CHCl_3$ 1735, 1640–1660$cm^{-1}$ |
| 12 | cyclohexanone dimethyl hydrazone | formic acid | 2-isocyano-3-phenylpropionic acid methyl ester | N- 1-[N-(dimethylamino)-formamido]cyclohexyl-carbonyl phenylalanine methyl ester, m.p. 80 – 83° C |
| 13 | cyclohexanone dimethyl hydrazone | p-nitrobenzoic acid | 2-isocyano-3-phenylpropionic acid | N- 1-[N-(dimethylamino)-p-nitrobenzamido]cyclo-hexylcarbonyl phenyl- |

TABLE 1-continued

| Ex. | Hydrazone of Formula 11 | Acid of Formula R³X | Isonitrile (R⁶NC) | Product of Formula 1 |
|---|---|---|---|---|
| 14 | isobutyraldehyde dimethyl hydrazone | formic acid | methyl ester ethyl isocyanoacetate | alanine methyl ester, m.p. 116 – 117° C N-[N-(dimethylamino)-N-formyl -DL-valyl]glycine ethyl ester, b.p. 150 – 153° C/0.1 mm, $\nu_{max}$Film 3300, 1745, 1670 cm$^{-1}$. |
| 15 | cyclohexanone dimethyl hydrazone | formic acid | ethyl isocyanoacetate | N- 1-[N-(dimethylamino)-formamido]cyclohexylcarbonyl glycine ethyl ester, m.p. 87 – 89° C $\nu_{max}$CHCl$_3$ 1732, 1658 cm$^{-1}$. |
| 16 | cyclohexanone dimethyl hydrazone | N-carbobenzoxy-glycylglycine | ethyl isocyanoacetate | N-[1- 1-[N-(carboxy-glycyl)glycyl]-2,2-dimethylhydrazino cyclohexylcarbonyl]glycine N-benzyl ethyl diester m.p. 138 – 139° C, $\nu_{max}$CHCl$_3$ 1720, 1655 cm$^{-1}$. |
| 17 | cyclohexanone dimethyl hydrazone | benzoic acid | ethyl isocyanoacetate | N- 1-[N-(dimethylamino)-benzamido]cyclohexylcarbonyl glycine ethyl ester, m.p. 90 – 92° C, $\nu_{max}$CHCl$_3$ 1730, 1660, 1630 cm$^{-1}$. |
| 18 | cyclohexanone dimethyl hydrazone | p-nitrobenzoic acid | ethyl isocyanoacetate | N- 1-[N-(dimethylamino)-p-nitrobenzamido]cyclohexylcarbonyl glycine methyl ester, m.p. 86 – 88° C, $\nu_{max}$CHCl$_3$ 1730, 1660, 1640 cm$^{-1}$. |
| 19 | ethyl acetoacetate dimethyl hydrazone | p-nitrobenzoic acid | ethyl isocyanoacetate | N-(carboxymethyl)-3-[N-(dimethylamino)-p-nitrobenzamido]-3-methylsuccinamic acid diethyl ester, m.p. 90 – 94° C, $\nu_{max}$CHCl$_3$ 1725, 1665 cm$^{-1}$. |
| 20 | cyclohexanone dimethyl hydrazone | formic acid | 2-isocyano-3-phenylpropionic acid methyl ester | N- 1-[N-(dimethylamino)-formamido]cyclohexylcarbonyl -DL-phenylalanine methyl ester, m.p. 84–86° C, $\nu_{max}$CHCl$_3$ 1735, 1660 cm$^{-1}$. |
| 21 | isobutyraldehyde dimethyl hydrazone | ±-butoxycarbonyl-glycine | 2-isocyano-4-methylthio-butyric acid ethyl ester (described in Example 4) | N- N-[N-(carboxyglycyl)-N-(dimethylamino-DL-valyl]] DL-methionine N-±-butyl ethyl diester, nmr (CDCl$_3$) δ 0.90 (d, J=7,3H), 1.05 (d, J=7,3H), 1.30 (2×t, J=7,3H), 2.10 (2×s,3H), 2.56 (2×s, 6H) |
| 22 | isobutyraldehyde dimethyl hydrazone | formic acid | 2-isocyano-4-methylthio-butyric acid ethyl ester | N-[N-(dimethylamino)-N-formyl-DL-valyl]-DL-methionine ethyl ester, nmr (CDCl$_3$) δ 0.95 (d, J=6.5,3H), 1.03 (d, J=6.5, 3H), 1.26 (+, J=7,3H), 2.10 (3H), 2.58 (6H) |
| 23 | isovaleraldehyde dimethyl hydrazone | ±-butoxycarbonylglycine | 2-isocyano-4-methylthio-butyric acid ethyl ester | N-(N-[N-(carboxyglycyl)-N-(dimethylamino)-DL-leucyl])-DL-methionine N-±-butyl ethyl diester, nmr (CDCl$_3$ δ 0.98 (d, J=5,6H), 1.26 (2+, J=7, 3H), 1.46(9H), 2.11(2s, 3H), 2.56(6H) |
| 24 | 1-(cyclohexylideneamino)piperidine | formic acid | ethyl isocyanoacetate | N-[1-(N-piperidinoformamido)cyclohexylcarbonyl]glycine ethyl ester, m.p. 119 – 120° C, $\nu_{max}$CHCl$_3$ 1730, 1655 cm$^{-1}$. |
| 25 | 1-(cyclohexylideneamino)piperidine | p-nitrobenzoic acid | ethyl isocyanoacetate | N- 1-[(p-nitro-N-piperidino)benzamido]cyclohexylcarbonyl glycine ethyl ester, m.p. 133 – 135° C, $\nu_{max}$CHCl$_3$ 1730, 1660 cm$^{-1}$. |
| 26 | isobutyraldehyde dimethyl hydrazone | ±-butoxycarbonyl-phenylalanine | ethyl, socyanoacetate | N- N-[N-(carboxyphenylalanyl)-N-(dimethylamino)-DL-valyl] glycine N-±-butyl ethyl diester, separable into two isomers by chromatography (SiO$_2$), isomer A: [α]$_D^{25}$ = −66.9° (CHCl$_3$), nmr (CDCl$_3$) δ 0.91 & 1.04 (6H), 1.29 (3H); Isomer B: [α]$_D^{24}$ = +40.0° (CHCl$_3$), nmr (CDCl$_3$) δ 0.75 & |

| Ex. | Hydrazone of Formula II | Acid of Formula R³X | Isonitrile (R⁶NC) | Product of Formula I |
|---|---|---|---|---|
| | | | | 1.03 (6H), 1.28 (3H). |

EXAMPLE 27

3-[N-(Dimethylamino)formamido]-3-methyl-2,5-dioxo-1-pyrrolidineacetic acid ethyl ester (III; and R¹ and R² = CH₃, R³ = CHO, R⁵ =CH₃ and R⁷ = H)

A solution of the hydrazone of formula II, ethyl acetoacetate dimethylhydrazone (13.7g., 0.08 mole), the acid of formula R³X, formic acid (3.1 ml, 0.08 mole) and the isonitrile of formula R⁶ NC, ethyl isocyanoacetate (9.1 g, 0.08 mole) in dry methylene chloride (25 ml) is stirred at room temperature until completion of the reaction. [In this case the reaction is complete after 21 hr. as determined by tlc using slica gel plates and a solvent system of benzeneethyl acetate (1:1)]. The mixture is diluted with ethyl acetate (200 ml) and 4N NH₄OH (100 ml). The organic layer is separated, washed with water, dried (MgSO₄) and concentrated under reduced pressure. The oily residue is crystallized from hexane-methylene chloride to give the title compound, m.p. 89° – 92° C., $\nu_{max}^{CHCl}$ 1785, 1740, 1715, 1665 cm⁻¹.

EXAMPLE 28

3-(p-Chloro-N-piperidinobenzamido)-3-methyl-2,5-dioxo-1-pyrrolidineacetic acid ethyl ester (III; R¹ and R² = (CH₂)₅, R³ = p-chlorophenyl, R⁵ =CH₃ and R⁷ = H)

A solution of the hydrazone of formula II, ethyl acetoacetate piperidinehydrazone (21.2 g, 0.1 mole), ethyl isocyanoacetate (11.3 g, 0.1 mole) and p-chlorobenzoic acid (15.6 g, 0.1 mole) in dry methylene chloride (50 ml) are stirred at reflux temperature for 7 days. The solution is diluted with methylene chloride (50 ml), and washed with 0.5 N ammonium hydroxide (50 ml), water (50 ml), and saturated sodium chloride solution (50 ml). The organic phase phase is dried (Na₂SO₄) and concentrated. The resulting oil and anhydrous potassium carbonate (20 g) in chloroform (200 ml) is heated at reflux temperature for 4 hr. The solution is filtered and the filtrate poured onto a column of silica gel (400 g). Elution with ethyl acetate-chloroform (1:3) affords the title compound having m.p. 153° – 155° C. after recrystallization from methylene chloride-hexane.

EXAMPLE 29

3-(2,2-Dimethylhydrazino)-3-methyl-2,3-dioxo-4-phenyl-1-pyrrolidineacetic acid ethyl ester III; R¹ and R² = CH₃, R³ = H, R⁵ = CH₃ and R⁷ = phenyl)

By following the procedure of Example 7 but replacing isobutyraldehyde dimethylhydrazone with an equivalent amount of ethyl-α-phenylacetoacetate dimethylhydrazone, described in Example I, then the title compound, m.p. 108° – 109° C., $\nu_{max}^{CHCl}$ 1770, 1738, 1700 cm⁻¹, is obtained.

By following the procedures of Example 27, 28 or 29 and using the appropriate hydrazone of formula II, acid of formula R³X and isonitrile of formula R⁶NC then other compounds of formula III are obtained. Examples of such compounds of formula III are listed in Table II together with the hydrazone, acid and isonitrile required for their preparation.

TABLE II

| Ex. | Hydrazone of Formula II | Acid of Formula R³X | Isonitrile (R⁶NC) | Product of Formula III |
|---|---|---|---|---|
| 30 | ethyl acetoacetate dimethyl hydrazone | acetic acid | ethyl isocyanoacetate | 3-[N-(dimethylamino)-acetamido]-3-methyl-2,5-dioxo-1-pyrrolidine-acetic acid ethyl ester m.p. 112 – 115° C. |
| 31 | ethyl acetoacetate dimethyl hydrazone | benzoic acid | ethyl isocyanoacetate | 3-[N-(dimethylamino)-benzamido]-3-methyl-2,5-dioxo-1-pyrrolidine-acetic acid ethyl ester, m.p. 100 – 102° C. |
| 32 | ethyl acetoacetate dimethyl hydrazone | p-nitro-benzoic acid | ethyl isocyanoacetate | 3-[N-(dimethylamino)-p-nitrobenzamido ]-3-methyl-2,5-dioxo-1-pyrrolidineacetic acid ethyl ester, m.p. 179 – 182° C. |
| 33 | ethyl acetoacetate dimethyl hydrazone | p-chlorobenzoic acid | ethyl isocyanoacetate | 3-[p-chloro-N-(dimethyl-amino)benzamido]-3-methyl-2,5-dioxo-1-pyrrolidine-acetic acid ethyl ester, m.p. 123 – 125° C. |
| 34 | 3-(piperidinoimino)-butyric acid methyl ester (described in Example 2) | formic acid | ethyl isocyanoacetate | 3-methyl-2,5-dioxo-3-(N-piperidinoformamido)-1-pyrrolidineacetic acid ethyl ester, m.p. 89 – 92° C. |
| 35 | 3-(piperidinoimino)-butyric acid methyl ester | benzoic acid | ethyl isocyanoacetate | 3-methyl-2,5-dioxo-3-(N-piperidinobenzamido)-1-pyrrolidineacetic acid ethyl ester, m.p. 140 – 144° C. |
| 36 | 3-(piperidinoimino)-butyric acid | p-nitrobenzoic acid | ethyl isocyanoacetate | 3-methyl-3-[p-nitro-N-piperidino)benzamido]-2,5-dioxo-1-pyrrolid- |

TABLE II-continued

| Ex. | Hydrazone of Formula II | Acid of Formula R³X | Isonitrile (R⁶NC) | Product of Formula III |
|---|---|---|---|---|
|  | methyl ester |  |  | ineacetic acid ethyl ester, m.p. 232 – 235° C. |
| 37 | 3-(morpholino-imino)butyric acid methyl ester (described in | formic acid | ethyl iso-cyanoacetate | 3-methyl-3-(N-morpholinoformamido)-2,5-dioxo-1-pyrrolidineacetic acid ethyl ester, m.p. 148 – 149° C. |
| 38 | 3-(morpholino-imino)butyric acid methyl ester (described in Example 2) | p-nitrobenzoic acid | ethyl iso-cyanoacetate | 3-[p-nitro-N-(morpholino)benzamido]-3-methyl-2,5-dioxo-1-pyrrolidineacetic acid ethyl ester, m.p. 237 – 238° C. |
| 39 | ethyl α-phenyl acetoacetate dimethyl hydrazone | formic acid | ethyl iso-cyanoacetate | 3-[N-(dimethylamino)-formamido]-3-methyl-2,5-dioxo-4-phenyl-1-pyrrolidineacetic acid ethyl ester, m.p. 123 – 124° C. |

EXAMPLE 40

3-[N-(Dimethylamino)-p-nitrobenzamido]-3-methyl-2,5-dioxo-1-pyrrolidineacetic acid ethyl ester III; $R^1$ and $R^2 = CH_3$, $R^3 =$ p-nitrophenyl, $R^5 = CH_3$ and $R^7$ H)

A solution of the compound of formula I, N-(carboxymethyl)-3-[N-dimethylamino)-p-nitrobenzamido]-3-methylsuccinamic acid diethyl ester (15.74 g, 0.035 mole), described in Example 19, and anhydrous potassium carbonate (15.0 g) in chloroform (100 ml) is heated at reflux for 90 min. After filtering the mixture the filtrate is concentrated. The residue is recrystallized from ethyl acetate to afford the title compound, identical to the product of Example 32.

The title compound is also obtained according to the procedure of this example in which the potassium carbonate is replaced by an equivalent amount of sodium carbonate or sodium or potassium hydroxide.

By following the procedure of this example and using the appropriately substituted compound of formula I in which $R^4$ represents CHR⁷COO-(lower alkyl) and $R^6$ represents CH₂C00-(lower alkyl) then the corresponding compounds of formula III, for example, those described in Examples 27 to 39, are obtained.

EXAMPLE 41

N-Cyclohexyl-4-(dimethylaminoformamido)-4-methylglutaramic acid (I; $R^1$ and $R^2 = CH_3$, $R^3 = CHO$, $R^4 = CH_2CH_2$ COOH, $R^5 = CH_3$ and $R^6 =$ cyclohexyl)

To 5.10 g (0.015 moles) of the corresponding ethyl ester of the title compound, described in Example 5 in 50 ml. of dry methanol, a solution of 1.68 g (0.030 moles) of potassium hydroxide in 5 ml. of dry methanol is added. The mixture is stirred for 6 hr. at room temperature. The mixture is concentrated under reduced pressure, cooled and rendered acidic (pH = 4) with dil. HCl. The resulting gum is taken up in chloroform. The chloroform extract is washed with water, dried (MgSO₄), and concentrated. The residue is crystallized from methylene chloride-ether to afford the title compound, m.p. 221°–222° C.

EXAMPLE 42

N-[N-(Dimethylamino)-N-(N-formylglycyl)]-DL-valyl -glycine (I; $R^1$ and $R^2 = CH_3$, $R^3 =$ COCH₂NHCHO, $R^4 = CH(CH_3)_2$, $R^5 =$ H and $R^6 =$ CH₂COOH)

A mixture of N- [N-(dimethylamino)-N-(N-formylglycyl)]-DL-valyl glycine ethyl ester (6.618 g, 0.020 moles), described in Example 6, and IN NaOH (30 ml) is stirred at room temperature for 90 min. The solution is cooled, rendered acidic with dilute HCl and extracted with chloroform. The extract is washed with brine, dried (MgSO₄) and concentrated. The residue is purified by chromatography on silica gel using methanol-chloroform (8:2) as the solvent system. The eluate is concentrated and crystallization of the residue from acetone-isopropyl ether affords the title compound, m.p. 157° – 158° C.

By following the procedure of Examples 41 or 42 other compounds of formula I in which the $R^4$ or $R^6$ radical includes an ester may be transformed to their corresponding acids. Examples of such acids prepared in this manner are listed in Table III. In these cases the ester used as starting material is indicated by the example in which it is prepared.

TABLE III

| EXAMPLE | No. of Example in Which Starting Material is Prepared | Product |
|---|---|---|
| 43 | 9 | N-cyclohexyl-4-[N-(dimethylamino)benzamido]-4-methylglutaramic acid, m.p. 118 – 119° C |
| 44 | 11 | N-[N-(dimethylamino)-N-formyl-DL-valyl]phenylalanine, m.p. 133 – 136° C |
| 45 | 12 | N- 1-[N-(dimethylamino)-formamido]cyclohexylcarbonyl - phenylalanine, m.p. 156 – 157° C |
| 46 | 14 | N-[N-(dimethylamino)-N-formyl-DL-valyl]glycine, m.p. 133 – 135° C |
| 47 | 15 | N- 1-[N-(dimethylamino)- |

TABLE III-continued

| EXAMPLE | No. of Example in Which Starting Material is Prepared | Product |
|---|---|---|
| | | formamido]cyclohexylcarbonyl-glycine, m.p. 139 – 142° C |

EXAMPLE 48

N- [N-(dimethylaino)-N-(N-formylglyclyl)]-DL-valyl-glycinamide (I; $R^1$ and $R^2$ = $CH_3$, $R^3$ = $COCH_2NHCHO$, $R^4$ = $CH(CH_3)_2$, $R^5$ = H and $R^6$ = $CH_2CONH_2$)

A saturated solution of ammonia in anhydrous methanol (100 ml) is added with cooling to N- [N-(dimethylamino)-N-(N-formylglycyl)]-DL-valyl glycine ethyl ester (12.81 g) described in Example 6. The mixture is stirred at room temperature for 4 days. The solvent is removed and the residue subjected to chromatography on silica gel. Elution with chloroform-methanol (98.2) affords the title compound which, after crystallization from acetone, has m.p. 165° – 168° C.

In the same manner but replacing N- [N-dimethylamino)-N-(N-formylglycyl)]-DL-valyl glycine ethyl ester with an equivalent amount of N-[N-(dimethylamino)-N-formyl-DL-valyl]-DL-phenylalanine methyl ester (Example II), N- N-[N-(carboxyglycyl)-N-(dimethylamino)-DL-leucyl]-DL-methionine N-t-butyl ethyl diester (Example 23), or N-[-(p-amino-N-piperidinobenzamido)cyclohexylcarbonyl]glycine ethyl ester Example 48), then N-[N-dimethylamino)-N-formyl-DL-valyl]-DL-phenylalaninamide, m.p. 147°-156° C, N-N-[N-(carboxyglycyl)-N-(dimethylamino)-DL-leucyl] -DL-methioninamide N-t-butyl ester, separated by chromatography on silica gel into Isomer A, m.p. 84° –89° C and Isomer B, m.p. 80°-90° C, and 2-[1-(p-amino-N-piperidinobenzamido)cyclohexanecarboxamido]acetamide, m.p. 198° – 201° C, are obtained, respectively.

EXAMPLE 49

N- 1-[p-Amino-N-(dimethylamino)benzamido]cyclohexylcarbonyl-DL-phenylalanine methyl ester (1; $R^1$ and $R^2$ =$CH_3$; $R^3$ = p-aminobenzoyl, $R^4$ and $R^5$ = $(CH_2)_5$ and $R^6$ = $CH(CH_2C_6H_5)COOCH_3$)

N- 1-[N-(Dimethylamino)-p-nitrobenzamido]cyclohexylcarbonyl-phenylalanine methyl ester (9.5 g), described in Example 13, in 20 ml. of dry methanol is hydrogenated with 5% palladium on charcoal. Thereafter, the catalyst is collected on a filter pad. The filtrate is concentrated and the residue crystallized from acetone-isopropyl ether to give the title compound, m.p. 138°–139° C.

In the same manner but replacing N- 1-(dimethylamino)-p-nitrobenzamido]cyclohexylcarbonyl glycine methyl ester (Example 18), or N- 1-[(p-nitro-N-piperidino)benzamido)]cyclohexylcarbonyl glycine ethyl ester (Example 25), then N- 1-[p-amino-N-(dimethylamino)benzamido]cyclohexylcarbonyl glycine ethyl ester, m.p. 69° – 71° C, and N- 1-(p-amino-N-piperidinobenzamido)cyclohexylcarbonyl glycine ethyl ester, m.p. 92° – 96° C, are obtained, respectively.

EXAMPLE 50

N-[N-(Dimethylamino)-N-(isocyanoacetyl)-DL-valyl]glycine ethyl ester (I; $R^1$ and $R^2$ = $CH_3$, $R^3$ = $COCH_2NC$, $R^4$ = $CH(CH_3)_2$, $R^5$ = H and $R^6$ = $CH_2COOC_2H_5$)

A solution of N- [N-(dimethylamino)-N-(N-formylglycyl)]-DL-valyl glycine ethyl ester (4.0 g), described in Example 6, in dry methylene chloride (12 ml) is placed in a 3-neck flask fitted with mechanical stirrer, reflux condenser and drying tube (KOH). Redistilled triethylamine is then added (5.08 ml) followed by dropwise addition of a solution of phosgene in benzene (12 ml. of a 12.5% solution). The mixture is stirred an additional 30 min. at room temperature, the precipitate is then filtered off, the filtrate concentrated under reduced pressure to dryness (at temperature < 40° ). The residue is diluted with anhydrous benzene (40 ml) and filtered once more. The filtrate is evaporated to dryness and the residue purified by column chromatography using silica gel. Elution with benzene-ethyl acetate (1:1) provides the isonitrile as a yellow solid. To remove the color the material is dissolved in benzene and the solution is filtered through a short column of alumina (Activity II. The fractions containing the isonitrile are pooled and the solvent removed at low temperature (<40° ) under reduced pressure the residue if triturated with anhydrous diethylether to give the title compound, m.p. 119-120.5° C.

By following the procedure of Example 50 but replacing N- [N-(dimethylamino)-N-(N-formylglycly)]-DL-valyl glycine ether ester with an appropriately substituted compound of formula I in which $R^3$ represents $COCH_2NHCHO$, prepared by the procedure of Example 6 or 7, then the corresponding compounds of formula I in which $R^3$ is $COCH_2NC$ are obtained. For example, N- [N-(dimethylamino)-N-(N-formylglycyl)]-DL-leucyl -DL-methionine ethyl ester gives N-[N-(diethylamino)-4-(isocyanoacetyl)-DL-leucyl]-DL-methionine ethyl ester.

We claim:

1. N- [N-(Dimethylamino-N-(N-formylglycyl)]-DL-valyl -glycine ethyl ester.
2. N-[(N-Dimethylamino)-DL-valyl]glycine ethyl ester.
3. N-[1- 1-[N-(Carboxyglycyl)glycyl]-2,2-dimethylhydrazone cyclohexylcarbonyl]glycine N-benzyl ethyl diester.
4. N- N-[N-(Carboxyglycyl)-N-(dimethylaino-DL-valyl] -DL-methionine N-t-butyl ethyl diester.
5. N-[N-(Dimethylamino)-N-formyl-DL-valyl]-DL-methionine ethyl ester.
6. N- N-[N-(Carboxyglycyl)-N-(dimethylamino)-DL-leucyl] -DL-methionine N-t-butyl ethyl diester.
7. N- N-[N-(Carboxyphenylalanyl)-N-(dimethylamino)-DL-valyl] glycine N-t-butyl ethyl diester.
8. N- [N-(Dimethylamino)-N-(N-formylgycyl)]-DL-valyl -glycine.
9. N- [N-(Dimethylamino)-N-(N-formylglycyl)]-DL-valyl -glycinamide.
10. N- N-[N-(Carboxyglycyl)-N-(dimethylamino)-DL-leucyl] -DL-methioninamide N-t-butyl ester.

* * * * *